(12) United States Patent
Shalaby

(10) Patent No.: US 7,694,813 B2
(45) Date of Patent: Apr. 13, 2010

(54) PACKAGE COMPONENTS FOR RADIOCHEMICAL STERILIZATION

(75) Inventor: Shalaby W. Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 1244 days.

(21) Appl. No.: 11/228,719

(22) Filed: Sep. 16, 2005

(65) Prior Publication Data

US 2007/0065334 A1   Mar. 22, 2007

(51) Int. Cl.
*A61L 2/08* (2006.01)

(52) U.S. Cl. .................. 206/438; 206/439; 206/528; 422/22; 422/28; 422/292

(58) Field of Classification Search .............. 422/22, 422/28, 32, 292, 294; 250/455.11; 206/438, 206/439, 528
See application file for complete search history.

(56) References Cited

U.S. PATENT DOCUMENTS

| | | | |
|---|---|---|---|
| 5,422,068 A | 6/1995 | Shalaby et al. | |
| 6,462,169 B1 * | 10/2002 | Shalaby | 528/354 |
| 2003/0069535 A1 * | 4/2003 | Shalaby | 604/48 |

\* cited by examiner

*Primary Examiner*—Sean E Conley
(74) *Attorney, Agent, or Firm*—Leigh P Gregory

(57) ABSTRACT

This invention deals with package components for radiochemical sterilization of medical or pharmaceutical products consisting of a hermetically sealed foil pack containing (1) a solid device, as in absorbable sutures and meshes, in a perforated holder or a liquid formulation in a sealed, flexible dispenser, as in absorbable cyanoacrylate-based tissue adhesive; (2) a microparticulate, unstabilized polyformaldehyde as a source of radiolytically generated formaldehyde encased in a sealed pouch comprising a porous, non-woven or woven fabric; and (3) a nitrogenous compound capable of reacting with residual formaldehyde, such as melamine or urea, that is encased in a sealed pouch comprising a porous, non-woven or woven fabric.

26 Claims, 2 Drawing Sheets

US 7,694,813 B2

PACKAGE COMPONENTS FOR RADIOCHEMICAL STERILIZATION

FIELD OF THE INVENTION

This invention relates to specially tailored package components for radiochemically sterilized (RC-Sd) medical devices in a hermetically sealed foil pack using a combination of low-dose, high-energy radiation and radiolytically generated gaseous formaldehyde, wherein said components include a solid polymeric source of formaldehyde in a porous carrier, a perforated device holder, and a solid reactive absorbent to remove residual formaldehyde.

BACKGROUND OF THE INVENTION

Radiochemical sterilization (RC-S) was first disclosed by this inventor in U.S. Pat. No. 5,422,068 and frequently described as the first novel approach to medical device sterilization since the early use of chemical sterilization in the presence of formaldehyde or ethylene oxide (Et-O) and high-energy radiation in the presence of gamma radiation or electron beam. It provides the medical device industry with a unique, hybrid process encompassing the attributes of chemical and radiation sterilization (RS) without the drawbacks associated with the use of the parent processes. Limitations on use of the most commonly used methods (namely, traditional RS and Et-O) have grown in the past three decades because of (1) degradation or undesirable changes in the properties of certain polymeric devices, such as those made from absorbable polyesters and polypropylene, caused by gamma radiation; (2) ineffective sterilization of simple and complex devices with Et-O and associated device recalls; and (3) toxic and explosive nature of Et-O. In contrast, the RC-S method combines the attributes of chemical sterilants and high-energy radiation and it entails (1) terminal sterilization of devices in a hermetically sealed package; (2) use of precisely generated formaldehyde through controlled radiolytic (caused by controlling the mass of the formaldehyde precursor and radiation dose) degradation of a solid polyformaldehyde insert to achieve surface sterility; and (3) less than 40% of the traditional radiation dose can be used to achieve surface and bulk device sterility—the radiation penetrates the mass of the device to ensure bulk sterility while complementing the formaldehyde in securing surface sterility. The commercial application of RC-S to segments of the medical device industry based on absorbable polyesters will represent a major milestone in such a fast-growing field encompassing traditional and new surgical products and innovative constructs for tissue engineering. A logical extension of the RC-S application will be for polypropylene-based devices, such as sutures, syringes, and many types of diagnostic devices.

The first commercial application of this technology will be radiation sterilization of absorbable polymeric devices. The use of RC-S is expected to extend to (1) other radiation-sensitive, biostable devices, such as those made of polypropylene (e.g., sutures and syringes); and (2) multicomponent packages, including resterilizable surgical kits containing both absorbable and non-absorbable components. However, U.S. Pat. No. 5,422,068 failed to address certain package-related requirements for the successful commercial use of the RC-S technology, which include (1) using a specially prepackaged, solid polymeric precursor that allows maximum diffusion of the generated formaldehyde into the gaseous environment without hindering its fugacity; (2) using a specially designed device holder for insuring the free diffusion of the generated formaldehyde from its precursor to effectively interact with any microflora on the medical device surface; and (3) providing a mechanism for practically irreversible, gradual immobilization of the residual formaldehyde in the package shortly after inactivating any microflora about the device. And this provided the incentive to explore the use of the package components subject of this invention that permit meeting the three requirements noted above.

SUMMARY OF THE INVENTION

This invention deals with package components for radiochemical sterilization of medical and pharmaceutical products. In particular, this invention deals with a hermetically sealed package for use in radiochemical sterilization of at least one medical device therein comprising an essentially gas impervious, moisture impervious sealed outer sheet, preferably of laminated foil, a perforated folder for holding the individual device contained within the sealed outer sheet, a radiolytically depolymerizable microparticulate polyformaldehyde encased and retained in a first sealed porous pouch contained within the sealed outer sheet and a formaldehyde-reactive microparticulate compound encased and retained in a second sealed porous pouch contained within the sealed outer sheet. The radiochemical sterilization is achieve in the presence of (1) high energy radiation at a dose of less than 10 kGy, wherein said radiation comprises gamma rays or electron beam, or (2) high energy radiation at a dose of less than 5 MeV of X-rays.

Another general aspect of this invention addresses a hermetically sealed package for use in radiochemical sterilization of at least one medical device therein comprising an essentially gas impervious, moisture impervious sealed outer sheet, a perforated folder for holding the individual device contained within the sealed outer sheet, a radiolytically depolymerizable microparticulate polyformaldehyde encased and retained in a first sealed porous pouch and a formaldehyde-reactive microparticulate compound encased and retained in a second sealed porous pouch, wherein (1) the perforated folder for holding the individual device is made of dried cellulosic material or polyolefin such as polyethylene; (2) the radiolytically depolymerizable polyformaldehyde microparticulate comprises unstabilized polyformaldehyde; (3) the formaldehyde reactive microparticulate compound comprises a reactive nitrogenous compound, capable of reacting with gaseous formaldehyde, selected from the group represented by urea and melamine; and (4) the porous pouch for encasing the polyformaldehyde or the formaldehyde-reactive compound is a non-woven fabric construct and preferably comprising a polyolefinic material selected from the group represented by polyethylene, polypropylene, and ethylene/propylene copolymer, alternatively, the pouch is made of a woven fabric construct made of polyethylene terephthalate.

In terms of application, this invention relates to a hermetically sealed, preferably laminated foil pack for use in radiochemical sterilization of at least one medical device therein comprising a perforated folder for holding the individual device, a radiolytically depolymerizable microparticulate polyformaldehyde encased and retained in a sealed porous pouch and a formaldehyde-reactive microparticulate compound encased and retained in a sealed porous pouch, wherein the device comprises an absorbable suture braid, an absorbable monofilament suture, an absorbable mesh, a partially absorbable vascular graft, an absorbable device for internal bone fixation, an absorbable stent, a metallic stent with an absorbable fibrous construct, and any vascular repair device comprising at least one absorbable component. Alternatively, the device comprises a medical device comprising polypropylene, as in monofilament polypropylene sutures.

A key aspect of this invention deals with a hermetically sealed preferably laminated foil pack for use in radiochemical sterilization of a least one medical device therein containing a radiolytically depolymerizable polyformaldehyde microparticulate encased and retained in a sealed porous pouch made of non-woven polyolefin or a woven polyethylene terephthalate, and a formaldehyde reactive microparticulate compound encased and retained in a sealed porous pouch similar to that used for the polyformaldehyde, wherein the radiochemical sterilization is achieved in the presence of (1) high energy radiation at a dose of less than 10 kGy, wherein said radiation comprises gamma rays or electron beam or (2) high energy radiation at a dose of less than 5 MeV of X-rays.

Another key aspect of this invention addresses a hermetically sealed preferably laminated foil pack for use in radiochemical sterilization of a least one medical device therein and said foil pack containing (1) a radiolytically depolymerizable polyformaldehyde microparticulate encased and retained in a sealed porous pouch made of a non-woven polyolefin or a woven polyester; (2) a formaldehyde reactive microparticulate compound encased and retained in a sealed porous pouch similar to that used for the polyformaldehyde; and (3) a medical device comprising a flexible sealed polymeric dispenser that is preferably made of a polyolefin, such as polyethylene and polypropylene containing a cyanoacrylate-based tissue adhesive. It is preferred that the cyanoacrylate-based tissue adhesive comprising methoxypropyl cyanoacrylate is contained in a sealed tapered flexible tube made of polyethylene or polypropylene. Alternatively, the tissue adhesive is contained in a sealed or tightly closed glass container. It is also preferred that the sealed laminated foil pack is further comprising a formaldehyde reactive nitrogenous compound, capable of reacting with gaseous formaldehyde, selected from the group represented by urea and melamine encased and retained in a sealed non-woven polyolefin or woven polyethylene terephthalate porous pouch.

A key aspect of this invention deals with a hermetically sealed preferably laminated foil pack for use in radiochemical sterilization of at least one medical device wherein the medical device comprises a flexible sealed polymeric dispenser containing a cyanoacrylate-based tissue adhesive. The sealed pack also contains unstabilized microparticulates of radiolytically depolymerizable polyformaldehyde encased and retained in a sealed non-woven polyolefin or a woven polyethylene terephthalate porous pouch.

BRIEF DESCRIPTION OF THE FIGURES OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention.

DETAILED DESCRIPTION OF THE PREFERRED EMBODIMENTS

Figure 1:
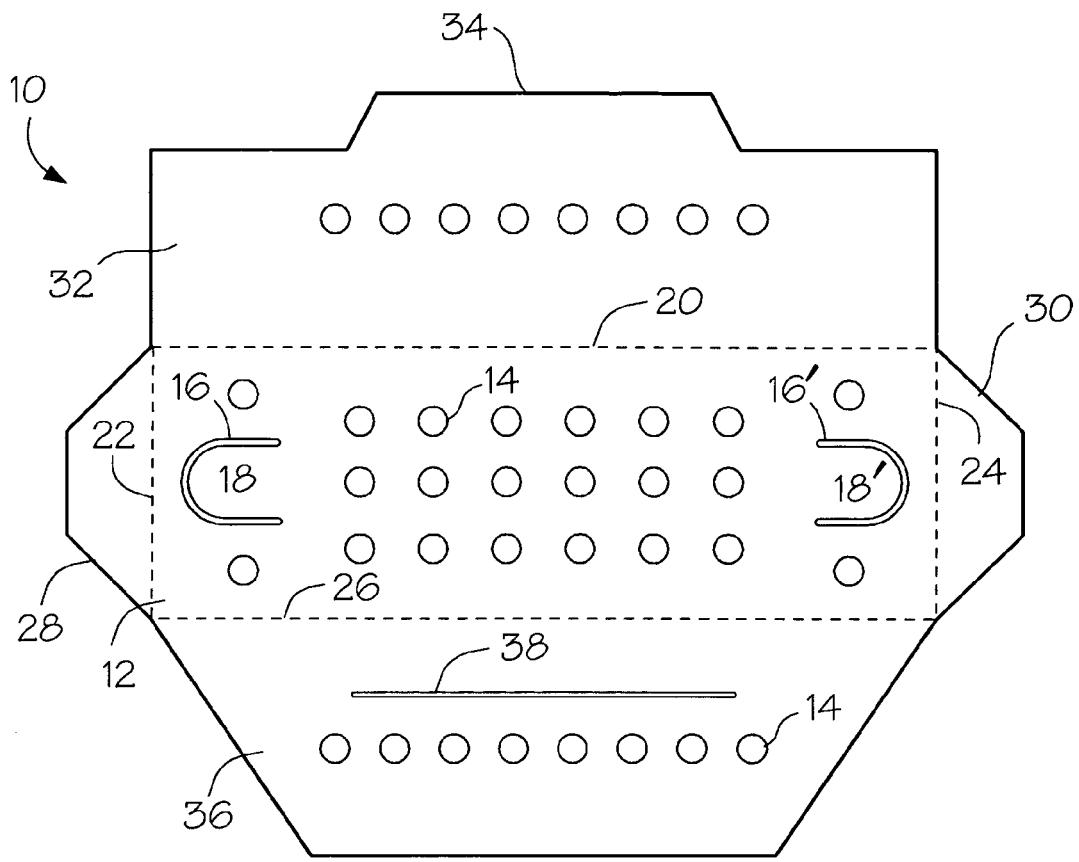
FIG. 1 is a top view of the perforated folder in accordance with the present invention in its unfolded configuration.

Radiochemical sterilization (RC-S) disclosed in U.S. Pat. No. 5,422,068 is, for the most part, based on the combined use of low-dose, high-energy radiation and radiolytically generated formaldehyde. However, successful practical application of the RC-S unique technology for sterilization of biomedical and pharmaceutical devices imposes other equally unique technological challenges that needed to be addressed. And this invention deals with practical and effective solutions to these challenges. The first among these challenges relates to the need to use a minimum amount of the formaldehyde precursor and its housing in a secure reservoir that will allow the radiolytically generated formaldehyde to escape freely to the gaseous environment and remain active for the desired period of time about the device to be sterilized. For this, the present invention calls for (1) the use of a highly radiolabile form of polyformaldehyde such as that known in the trade as unstabilized Celcon® M-90; (2) microparticulate solid polyformaldehyde with exceptionally high surface-to-volume ratio to allow the gaseous formaldehyde to escape freely into the gaseous environment in the package and about the device; (3) a hermetically sealed gas and moisture impervious, preferably foil, pack filled with dry, essentially inert gas, such as nitrogen or argon—this is to maintain the formaldehyde activity by eliminating its partitioning with traces of water or partial oxidation; (4) incasing the solid polyformaldehyde in a sealed, non-woven, porous fabric pouch (preferably made of Tyvek®) or woven, porous fabric pouch (preferably made of polyethylene terephthalate) that retain the solid but allow the formaldehyde to escape freely to the environment about the device; (5) a holder of the device that allows the formaldehyde to circulate freely about the device—for this, a holder, as in the case of a folder for surgical suture, is described in this invention as depicted in FIGS. 1-5 to have perforated walls wherein said folder can be made of a flexible polymer, such as polyethylene (or polypropylene) or dried cellulosic paper (this can also act as a desiccant); and (6) a packaging system that is impermeable to gases, such as formaldehyde—this is a laminated foil used in this invention to produce the hermetically sealed primary package for devices that are held in folders or secondary packages for prepackaged liquid tissue adhesive contained in sealed, flexible polymeric dispensers. The sealed package may also comprise a traditional desiccant, such as anhydrous silica or molecular sieve, contained in a permeable solid carrier. The second challenging area relates to minimizing or eliminating residual formaldehyde in the gaseous environment of the package shortly after deactivating any micro-organisms which may be present within the package. For this, the present invention discloses (1) a limited mass of the Celcon® M-90 to generate a sufficient, but not excessive, amount of gaseous formaldehyde to achieve sterility; (2) the surprising ability of Celcon® M-90 microparticulates to absorb part of the gaseous formaldehyde which subsequently polymerizes and becomes part of the solid precursor; and (3) the use of chemical compounds that have an exceptional propensity for reacting with free and accessible gaseous formaldehyde leading to its practical elimination from the gaseous environment about the device—for this, reactive nitrogenous compounds, such as melamine and urea, are encased in sealed porous pouches (similar to those used to house polyformaldehyde) and placed as package inserts in the primary package or secondary package for sutures/meshes, or liquid tissue adhesives, respectively.

A key aspect of this invention is the judicious selection of the articles to sterilize and focusing on those which cannot be effectively sterilized by other, more traditional means. Accordingly, this invention deals with the RC-S of (1) absorbable polyester-based sutures; (2) fully or partially absorbable fibrous vascular grafts; (3) fully or partially absorbable meshes for use in repairing tissue defects; and (4) fully or partially absorbable scaffolds for use in tissue engineering, or to allow natural tissue ingrowth. Obviously, all these forms of devices are known to degrade upon using the traditional radiation sterilization (RS) (at a nominal dose which may approach or exceed 25 kGy) or cannot be easily and effectively sterilized using ethylene oxide because of the complex geometries and associated problems of gas accessibility to achieve sterility and removal of residual toxic gases at the conclusion of the sterilization process.

Another key aspect of this invention deals with unique use of RC-S to sterilize cyanoacrylate-based tissue adhesive. These are known to undergo unwanted level of radiation-induced polymerization when the traditional radiation sterilization cycle of 25 kGy is used. When using RC-S, the liquid cyanoacrylate-based tissue adhesive is filled in a flexible dispenser (typically made of polyethylene or polypropylene) that is sealed under nitrogen and then placed in the new, hermetically sealed laminated foil pack described in this invention, as the secondary package.

This invention deals generally with a hermetically sealed, laminated foil pack for use in radiochemical sterilization of at least one medical device therein comprising a perforated folder for holding the individual device, a radiolytically depolymerizable microparticulate polyformaldehyde encased and retained in a sealed porous pouch and a formaldehyde-reactive microparticulate compound encased and retained in a sealed porous pouch, wherein the radiochemical sterilization is achieve in the presence of (1) high energy radiation at a dose of less than 10 kGy, wherein said radiation comprises gamma rays or electron beam, or (2) high energy radiation at a dose of less than 5 MeV of X-rays.

Another general aspect of this invention addresses a hermetically sealed, laminated foil pack for use in radiochemical sterilization of at least one medical device therein comprising a perforated folder for holding the individual device, a radiolytically depolymerizable microparticulate polyformaldehyde encased and retained in a sealed porous pouch and a formaldehyde-reactive microparticulate compound encased and retained in a sealed porous pouch, wherein (1) the perforated folder for holding the individual device is made of dried cellulosic material or polyolefin such as polyethylene; (2) the radiolytically depolymerizable polyformaldehyde microparticulate comprises unstabilized polyformaldehyde; (3) the formaldehyde reactive microparticulate compound comprises a reactive nitrogenous compound, capable of reacting with gaseous formaldehyde, selected from the group represented by urea and melamine; and (4) the porous pouch for encasing the polyformaldehyde or the formaldehyde-reactive compound is a non-woven fabric construct and preferably comprising a polyolefinic material selected from the group represented by polyethylene, polypropylene, and ethylene/propylene copolymer, alternatively, the pouch is made of a woven fabric construct made of polyethylene terephthalate.

In terms of application, this invention relates to a hermetically sealed, laminated foil pack for use in radiochemical sterilization of at least one medical device therein comprising a perforated folder for holding the individual device, a radiolytically depolymerizable microparticulate polyformaldehyde encased and retained in a sealed porous pouch and a formaldehyde-reactive microparticulate compound encased and retained in a sealed porous pouch, wherein the device comprises an absorbable suture braid, an absorbable monofilament suture, an absorbable mesh, a partially absorbable vascular graft, an absorbable device for internal bone fixation, and an absorbable stent. Alternatively, the device comprises a medical device comprising polypropylene, as in monofilament polypropylene sutures.

A key aspect of this invention deals with a hermetically sealed laminated foil pack for use in radiochemical sterilization of a least one medical device therein comprising a radiolytically depolymerizable polyformaldehyde microparticulate encased and retained in a sealed porous pouch made of non-woven polyolefin or a woven polyethylene terephthalate, and a formaldehyde reactive microparticulate compound encased and retained in a sealed porous pouch similar to that used for the polyformaldehyde, wherein the radiochemical sterilization is achieved in the presence of (1) high energy radiation at a dose of less than 10 kGy, wherein said radiation comprises gamma rays or electron beam or (2) high energy radiation at a dose of less than 5 MeV of X-rays.

Another key aspect of this invention addresses a hermetically sealed laminated foil pack for use in radiochemical sterilization of a least one medical device therein and said foil pack comprising (1) a radiolytically depolymerizable polyformaldehyde microparticulate encased and retained in a sealed porous pouch made of a non-woven polyolefin or a woven polyester; (2) a formaldehyde reactive microparticulate compound encased and retained in a sealed porous pouch similar to that used for the polyformaldehyde; and (3) a medical device comprising a flexible sealed polymeric dispenser that is preferably made of a polyolefin, such as polyethylene and polypropylene containing a cyanoacrylate-based tissue adhesive. It is preferred that the cyanoacrylate-based tissue adhesive comprising methoxypropyl cyanoacrylate contained in a sealed tapered flexible tube made of polyethylene or polypropylene. It is also preferred that the sealed laminated foil pack is further comprising a formaldehyde reactive nitrogenous compound, capable of reacting with gaseous formaldehyde, selected from the group represented by urea and melamine encased and retained in a sealed non-woven polyolefin or woven polyethylene terephthalate porous pouch.

A key aspect of this invention deals with a hermetically sealed laminated foil pack for use in radiochemical sterilization of at least one medical device wherein the medical device comprises a flexible sealed polymeric dispenser containing a cyanoacrylate-based tissue adhesive. The sealed pack also comprises unstabilized microparticulates of radiolytically depolymerizable polyformaldehyde encased and retained in a sealed non-woven polyolefin or a woven polyethylene terephthalate porous pouch.

Figure 2:
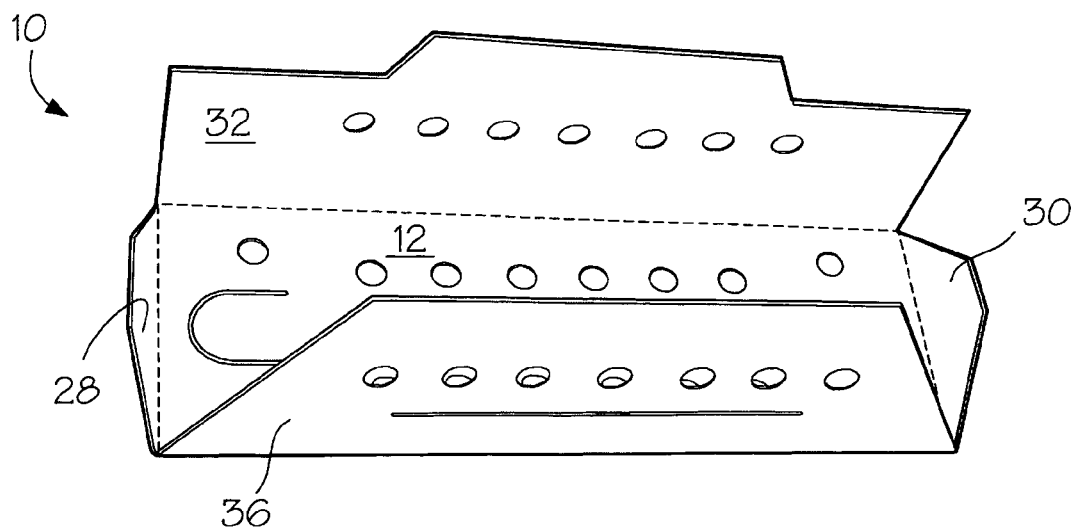
FIGS. 2-4 illustrate the folder of FIG. 1 as it is being folded.
Figure 3:
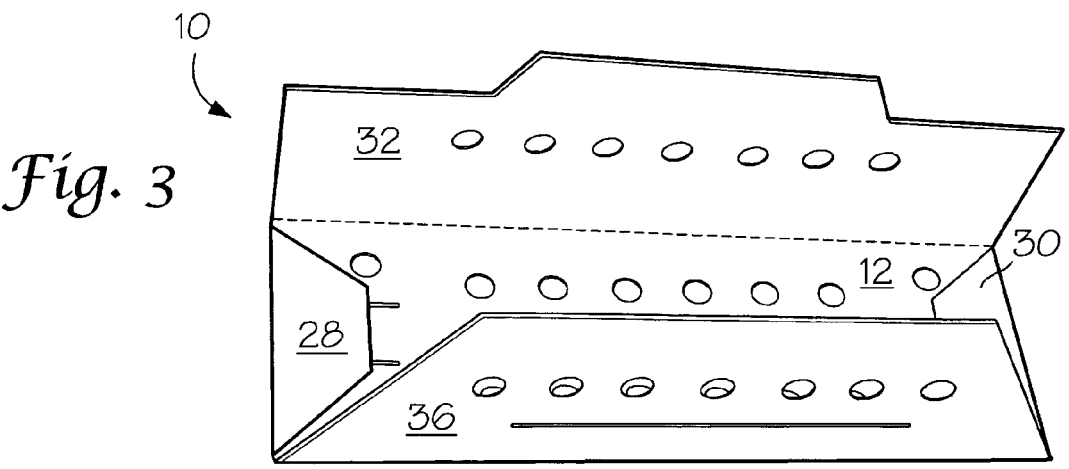
Figure 4:
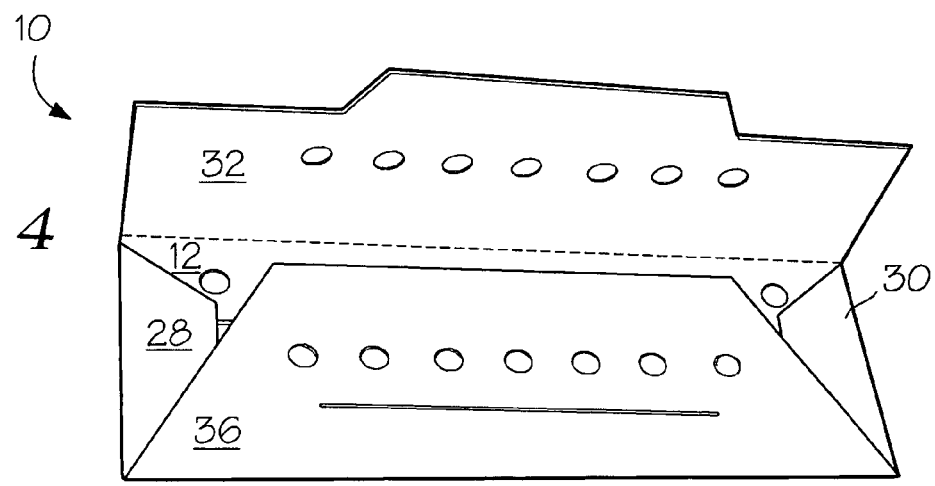
Figure 5:
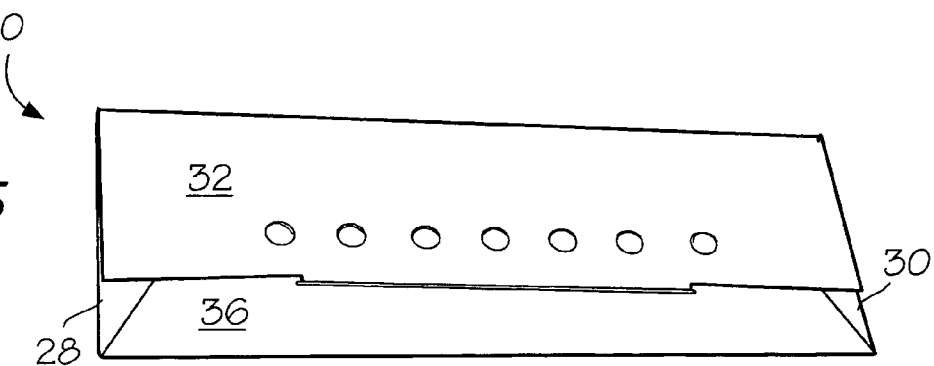
FIG. 5 shows the perforated folder of Figure in its folded and secured configuration.

For those embodiments of the present invention which employ a perforated folder for holding a medical device, a preferred folder is illustrated at FIGS. 1-5. FIG. 1 shows the preformed folder in its open, unfolded configuration. Base wall 12 includes numerous perforations 14 defined therein. Also defined in base wall 12 are U-shaped grooves 16 and 16'. These grooves define tabs 18 and 18' for holding a medical device such as a length of suture. The outer perimeter of the base wall 12 is defined by preformed creases 20, 22, 24, and 26. Side walls 28 and 30 extend outwardly from creases 22 and 24, respectively. Top wall 32 extends outwardly from crease 20, includes numerous perforations 14, and further defines flap 34. Top wall 36 extends outwardly from crease 26, includes numerous perforations 14, and notch 38 defined therein. FIG. 2 shows the folder as the side and top walls are being folded. As is better shown in FIGS. 3 and 4, side walls 28 and 30 are folded in toward the base wall 12 first. Then, top wall 36 is folded over the side walls and, finally, top wall 32 is folded over top wall 36. To secure the folder in its closed position flap 34 is inserted into notch 38. Thus, when the folder is closed, the perforations defined in the top walls and the base wall allow for the free flow of a desired gas around the contained medical device. As noted above, while the perforated folder of the present invention must be sufficiently stiff to hold the medical device in place and fold into its closed configuration, it may be formed of any suitable material, although cellulosic or polyolefinic materials are preferred.

Additional illustrative examples associated with this invention are outlined below:

Example 1

Radiochemical Sterilization of Polyglycolide (PG) Braided Sutures

A number of vacuum dried 27 inch lengths of size 2-0 braided sutures were individually placed in a predried, perforated paper folder as described in FIG. 1 and placed in four groups of 3"×5" laminated foil packs having a sealed, non-woven polyethylene (Tyvek®) porous pouch filled with microparticulates of unstabilized Celcon® M-90 polyformaldehyde (200 mg). The first group (I) contained the suture/folder and the Celcon pouch. Into the second group (II) of packs was placed a second sealed, non-woven Tyvek® pouch containing dry melamine microparticulate (20 mg). In the third group (III) of packs was placed a sealed, non-woven Tyvek® pouch containing dry microparticulate urea (20 mg). In the fourth group (IV) of packs was placed a spore strip having a spore count of $10^7$. Groups I to IV were prepurged twice with dry nitrogen and hermetically sealed. The sealed packs were gamma irradiated with about 5 kGy using a Co-60 source at a dose rate of 32 kGy/hr. Two weeks after the irradiation, the packs ere divided into separate groups and tested using standard techniques needed to determine (1) the residual formaldehyde in the package; (2) suture sterility; (3) reduction in spore count in the spore strip; and/or (4) retention of the suture tensile properties. An outline of the experimental design and summary of results are shown in Table I.

TABLE I

Outline of the Experimental Design and Results of Radiochemically Sterilized PG Braided Size 2-0 Sutures

| Experiment | Average Results for | | | |
|---|---|---|---|---|
| | Group I | Group II | Group III | Group IV |
| Residual formaldehyde package, μg | <10 | <2 | <2 | <10 |
| Suture sterility, % | 100 | 100 | 100 | 100 |
| Log reduction in spore count in spore strip | — | — | — | 7 |
| Suture breaking strength retention, % | >95 | >97 | >97 | >97 |

Example 2

Radiochemical Sterilization of Absorbable Cyanoacrylate-Based Tissue Adhesive Formulation Two types of methoxypropyl cyanoacrylate(MPC)-based tissue adhesive formulations, A and B, were packaged under nitrogen atmosphere in sealed polyethylene dispensers (volume=1 mL) with tapered necks. Each dispenser contained 0.4 mL of liquid formulation. Formulation A contained MPC, an absorbable polyester modifier and a trace amount of stabilizer to protect the formulation against premature anionic polymerization. In formulation B, the cyanoacrylate monomer consisted of a mixture of MPC and ethyl cyanoacrylate. Pairs of the dispensers containing formulation A or B were placed in groups of 3"×5" laminated foil packs, each containing a sealed non-woven polyethylene (Tyvek®) porous pouch filled with microparticulate of unstabilized Celcon® M-90 polyformaldehyde (200 mg). The first group (I-A and I-B for formulations A and B, respectively) contained the pairs of formulation A or B dispensers and the Celcon® pouch. Into the second group (II-A and II-B) of the packs was placed a second sealed, non-woven Tyvek® pouch containing dry melamine microparticulate (20 mg). In the third group (III-A and III-B) of packs was placed a sealed non-woven Tyvek® pouch containing dry microparticulate urea (20 mg). In the fourth group of packs (IV-A and IV-B) was placed a spore strip having a spore count of $10^7$. Groups I-A to IV-A and I-B to IV-B were purged with dry nitrogen and hermetically sealed. The sealed packs were gamma irradiated with about 5 kGy using a Co-60 source at a dose rate of 32 kGy/hr. Two weeks after irradiation, the packs were divided into separate groups and tested using standard techniques needed to determine (1) the residual formaldehyde in the package; (2) sterility of the liquid formulation and the outside surface of the polyethylene dispenser; (3) the reduction in spore count in the spore strip; and/or (4) retention of the tissue adhesive properties. An outline of the experimental design and summary of results are shown in Table II.

TABLE II

Outline of the Experimental Design and Results of Radiochemically Sterilized Cyanoacrylate-based Tissue Adhesive Formulations

| | Average Results for Formulation A Group | | | | Average Results for Formulation B Group | | | |
|---|---|---|---|---|---|---|---|---|
| | I-A | II-A | III-A | IV-A | I-B | II-B | III-B | IV-B |
| Residual formaldehyde, μg | 10 | <2 | <2 | <10 | <10 | <2 | <2 | <10 |
| Liquid adhesive Sterility, % | ◄—————————————— 100 ——————————————► | | | | | | | |
| Dispenser surface sterility, % | ◄—————————————— 100 ——————————————► | | | | | | | |
| Log reduction in spore count in spore strip | — | — | — | 7 | — | — | — | 7 |
| Increase in formulation viscosity, % | ◄—————————————— <40 ——————————————► | | | | | | | |
| Decrease in formulation adhesive joint strength, % | ◄—————————————— <10 ——————————————► | | | | | | | |

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all subranges of all ranges disclosed herein. These subranges are also useful in carrying out the present invention.

What is claimed is:

1. A hermetically sealed package for use in radiochemical sterilization of at least one medical device contained therein comprising:
    an essentially gas impervious, moisture impervious sealed outer sheet;
    a perforated folder contained within the sealed outer sheet for holding the medical device;
    a first sealed porous pouch contained within the sealed outer sheet and containing a radiolytically depolymerizable polyformaldehyde microparticulate; and
    a second sealed porous pouch contained within the sealed outer sheet and containing a formaldehyde-reactive microparticulate compound.

2. A hermetically sealed package as set forth in claim 1 wherein the outer sheet comprises a laminated foil.

3. A hermetically sealed package as set forth in claim 1 wherein the perforated folder comprises a dried cellulosic material.

4. A hermetically sealed package as set forth in claim 1 wherein the perforated folder comprises a polyolefinic material.

5. A hermetically sealed package as set forth in claim 4 wherein the perforated folder comprises polyethylene.

6. A hermetically sealed package as set forth in claim 1 wherein the radiolytically depolymerizable polyformaldehyde microparticulate comprises unstabilized polyformaldehyde.

7. A hermetically sealed package as set forth in claim 1 wherein the formaldehyde-reactive microparticulate compound comprises a reactive nitrogenous compound capable of reacting with gaseous formaldehyde selected from the group consisting of urea and melamine.

8. A hermetically sealed package as set forth in claim 1 wherein at least one of the first and second sealed porous pouches comprises a non-woven fabric construct comprising a polyolefinic material selected from the group consisting of polyethylene, polypropylene, and ethylene/propylene copolymer.

9. A hermetically sealed package as set forth in claim 1 wherein at least one of the first and second sealed porous pouches comprises a woven fabric construct comprising polyethylene terephthalate.

10. A hermetically sealed package as set forth in claim 1 wherein the medical device comprises an absorbable suture braid.

11. A hermetically sealed package as set forth in claim 1 wherein the medical device comprises an absorbable monofilament suture.

12. A hermetically sealed package as set forth in claim 1 wherein the medical device comprises an absorbable mesh.

13. A hermetically sealed package as set forth in claim 1 wherein the medical device comprises a partially absorbable vascular graft.

14. A hermetically sealed package as set forth in claim 1 wherein the medical device comprises an absorbable device for internal bone fixation.

15. A hermetically sealed package as set forth in claim 1 wherein the medical device comprises an absorbable stent.

16. A hermetically sealed package as set forth in claim 1 wherein the device is a metallic stent covered with an absorbable fibrous construct.

17. A hermetically sealed package as set forth in claim 1 wherein the medical device is a vascular repair device comprising at least one absorbable component.

18. A hermetically sealed package as set forth in claim 1 wherein the medical device is formed of polypropylene.

19. A hermetically sealed package as set forth in claim 1 wherein at least one of the first and second sealed porous pouches comprises a woven fabric construct comprising polyethylene terephthalate.

20. A hermetically sealed package for use in radiochemical sterilization of at least one medical device comprising:
   an essentially gas impervious, moisture impervious sealed outer sheet;
   a medical device contained within the sealed outer sheet;
   a first sealed porous pouch contained within the sealed outer sheet and containing a radiolytically depolymerizable polyformaldehyde microparticulate; and
   a second sealed porous pouch contained within the sealed outer sheet and containing a formaldehyde-reactive microparticulate compound.

21. A hermetically sealed package as set forth in claim 20 wherein the outer sheet comprises a laminated foil.

22. A hermetically sealed package as set forth in claim 20 wherein the medical device comprises a flexible sealed polymeric dispenser containing a cyanoacrylate-based tissue adhesive.

23. A hermetically sealed package as set forth in claim 22 wherein the cyanoacrylate-based tissue adhesive comprises methoxypropyl cyanoacrylate and wherein the flexible sealed polymeric dispenser comprises a polyolefin selected from polyethylene and polypropylene.

24. A hermetically sealed package as set forth in claim 20 wherein the radiolytically depolymerizable polyformaldehyde microparticulate comprises unstabilized polyformaldehyde.

25. A hermetically sealed package as set forth in claim 20 wherein the formaldehyde-reactive microparticulate compound comprises a reactive nitrogenous compound capable of reacting with gaseous formaldehyde selected from the group consisting of urea and melamine.

26. A hermetically sealed package as set forth in claim 20 wherein at least one of the first and second sealed porous pouches comprises a non-woven fabric construct comprising a polyolefinic material selected from the group consisting of polyethylene, polypropylene, and ethylene/propylene copolymer.

* * * * *